United States Patent
Zerle

(10) Patent No.: US 7,242,747 B2
(45) Date of Patent: Jul. 10, 2007

(54) METHOD FOR DETERMINING A GSM SUBSTANCE AND/OR A CHEMICAL COMPOSITION OF A CONVEYED MATERIAL SAMPLE, AND A DEVICE FOR THIS PURPOSE

(75) Inventor: Ludwig Zerle, Bogen (DE)

(73) Assignee: Mahlo GmbH & Co. KG, Saal/Donau (DE)

( * ) Notice: Subject to any disclaimer, the term of this patent is extended or adjusted under 35 U.S.C. 154(b) by 130 days.

(21) Appl. No.: 10/968,327

(22) Filed: Oct. 20, 2004

(65) Prior Publication Data

US 2005/0163282 A1   Jul. 28, 2005

(30) Foreign Application Priority Data

Oct. 21, 2003  (DE) ............................... 103 48 834
Sep. 3, 2004   (DE) ...................... 10 2004 042 769

(51) Int. Cl.
  *G01N 23/201* (2006.01)
(52) U.S. Cl. .......................................... 378/88; 378/90
(58) Field of Classification Search ................. 378/88, 378/90
  See application file for complete search history.

(56) References Cited

U.S. PATENT DOCUMENTS

| | | | | | |
|---|---|---|---|---|---|
| 4,779,621 A | * | 10/1988 | Mattson | ...................... | 600/431 |
| 5,420,905 A | * | 5/1995 | Bertozzi | ...................... | 378/88 |
| 5,600,700 A | * | 2/1997 | Krug et al. | .................. | 378/57 |
| 6,775,351 B2 | * | 8/2004 | Rinaldi et al. | ............. | 378/98.8 |

* cited by examiner

*Primary Examiner*—Edward J. Glick
*Assistant Examiner*—Thomas R. Artman
(74) *Attorney, Agent, or Firm*—Oblon, Spivak, McClelland, Maier & Neustadt, P.C.

(57) ABSTRACT

A method for determining a weight per unit area and/or a chemical composition of a conveyed material sample. From the analysis of a portion of an incident ionizing radiation, in particular an X-radiation, scattered from a material sample, a detector signal corresponding to the gsm substance and/or the chemical composition of the material sample is generated and used for determining the weight per unit area and/or the chemical composition of the material sample. A device for determining a weight per unit area and/or a chemical composition of a material sample has a compact measurement head arranged unilaterally with respect to the material sample. This measurement head includes an X-radiation source and a detector arrangement integrated into the measurement head of at least one X-ray detector connected to a voltage supply and an evaluation unit.

14 Claims, 1 Drawing Sheet

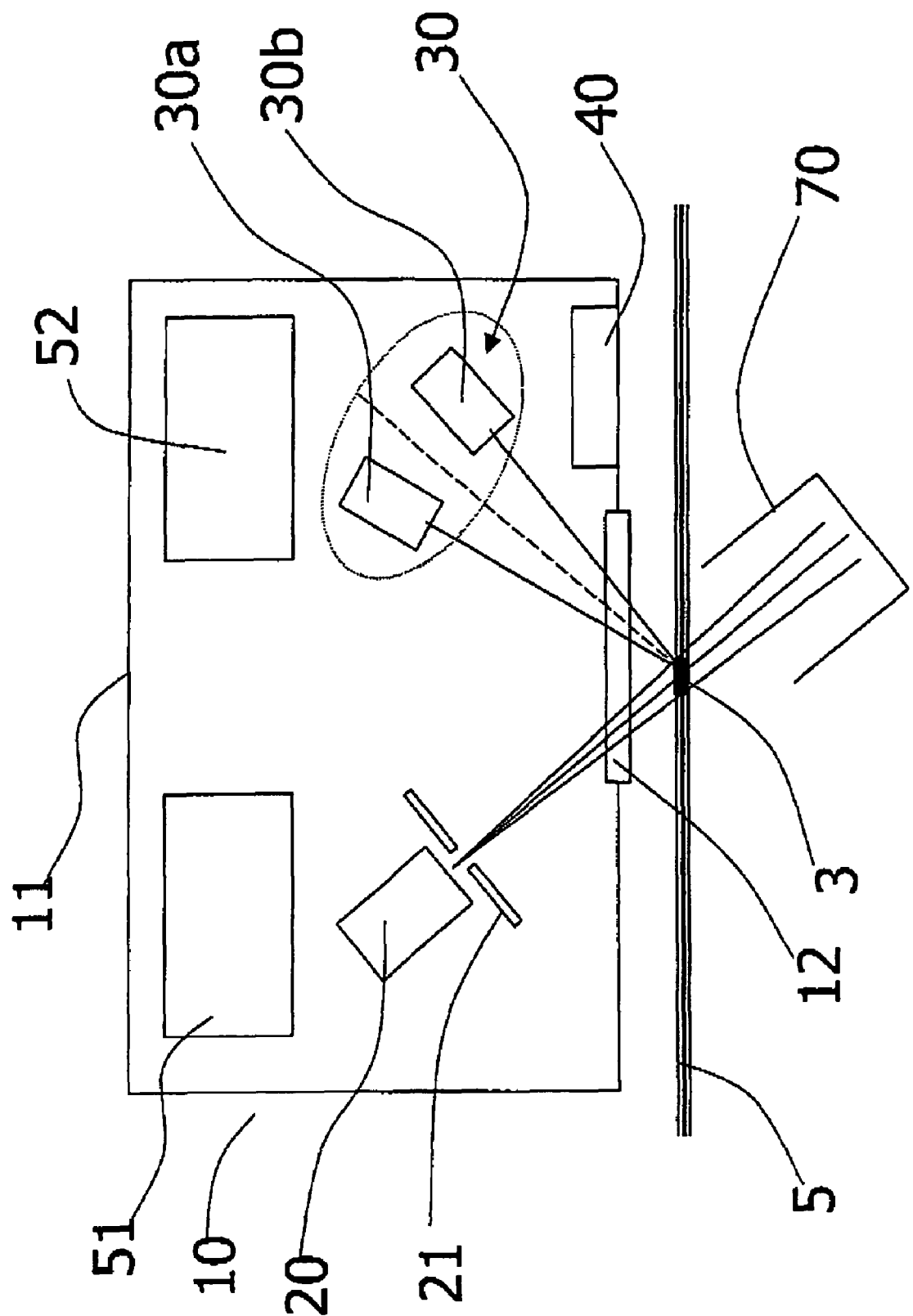

7,242,747 B2

METHOD FOR DETERMINING A GSM SUBSTANCE AND/OR A CHEMICAL COMPOSITION OF A CONVEYED MATERIAL SAMPLE, AND A DEVICE FOR THIS PURPOSE

A method for determining a weight per unit area and/or a chemical composition of a conveyed material sample, and a device for this purpose

BACKGROUND OF THE INVENTION

1. Field of the Invention

The invention relates to a method for determining a weight per unit area and/or a chemical composition of a conveyed material sample, and to a device for carrying out the method.

2. Discussion of the Background

For determining a weight per unit area (e.g., grams per square meter; $g/m^2$) and/or a chemical composition of material samples or material webs in conveyor and production plants partially operated at high speeds, absorption measurements are carried out according to the state of the art, using ionized radiation, in particular x-ray, gamma or particulate radiation. In this case, the webs or samples to be tested are passed through between a source of radiation and a detector arrangement placed opposite the source of radiation, and, in a transmission measurement, the intensity of the radiation absorption is determined. This radiation absorption depends on the weight per unit area of the webs and samples so that the mentioned characteristics of the webs and samples may be measured in a contact-free manner by means of this known method and corresponding devices.

A further possibility of measuring the weight per unit area of a material web or a sheet material consists in detecting scattered radiation. NDC Infrared Engineering and Adaptive Technologies, for example, are companies who use this method in their products by detecting back-scattered photons originating from a gamma radiation source, e.g. photons of the 59 keV line of the Am 241 isotope.

A systematic measurement error occurs in this method when the distance between the place where the particles of the incident ray are scattered and the location of the detector varies. Such a distance variation may occur due to a random fluttering movement of the material web, and also always occurs when the thickness of the measured product changes. In this case, purely geometric reasons cause the measurement signal to be influenced, and these reasons, if not corrected by additional independent measurements, will lead to an erroneous reproduction of the value of the weight per unit area. This systematic effect, however, may be limited when a large distance between the measured product and the detector is selected. But the distance may not be so large, for the purpose of maximizing the detection efficiency of the scattered radiation and lowering the associated statistical error of the detector with using, at the same time, the least possible intensity of the source of the incident ray. It is therefore important to correct the inaccuracies caused by distance variations in order to attain minimal measurement error at an economic cost.

In all known methods for measuring weights per unit area in which ionized radiation is used, the radiation originates from the decomposition of radioactive isotopes. In this case, the operating company is subjected to the radiation-protection regulation requiring the operating company to observe rest times even during a standstill of the plant, as well as being subject to elaborate safety measures.

The economic availability and the natural properties of radioactive nuclides and the ionized radiation thereof, e.g. half-life, type and energy distribution, strongly restrict the number of industrially usable preparations. In addition, using a single radionuclide may allow only a restricted functional range to be covered. Thus, the beta radiation of the frequently used nuclide Kr 85, for example, having an end-point energy of 687.4 keV, due to its absorption behaviour is well suited for determining weights per unit area of up to about 1000 $g/m^2$. Higher weights per unit area may no longer be detected with it in a satisfactory manner and are preferably measured with the nuclide Sr 90, in which in the consecutive decomposition of Y 90, a beta radiation of a higher energy and hence of a higher penetration occurs having an end-point energy of 2280.1 keV.

SUMMARY OF THE INVENTION

The object is thus to propose a method for determining the weight per unit area and/or a chemical composition of a material sample, and a device, which avoids the above-mentioned drawbacks to a large extent, which may be applied advantageously within the framework of a large-scale and highly productive manufacturing plant, which may be integrated in a simple manner and allow a precise measurement of the required material properties even under physically unfavourable conditions of large-scale production.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein the attached FIGURE is an illustration of a device for determining a weight per unit area and/or a chemical composition of a conveyed material sample.

DESCRIPTION OF THE EMBODIMENTS

The embodiments will now be described with reference to the accompanying drawing.

The method for determining a weight per unit area and/or a chemical composition of a conveyed material sample is characterized according to the invention in that the weight per unit area of the material sample and/or the chemical composition thereof is determined from analysis of a ray portion of an incident X-radiation, which ray portion is scattered from the material sample.

In contrast to the principle used in the state of the art for a transmission measurement of the X-radiation, scattering effects within the sample are used according to the invention, during which the incident radiation penetrates into the sample material and is back-scattered by the material. In this case, the back-scattered radiation portion contains information on the weight per unit area of the sample and the chemical composition thereof and is received by a detector, and the detector signal is evaluated.

Here, the X-radiation from a source of radiation is appropriately directed onto a radiation spot of the material sample, and the scattered radiation generated in the material sample due to inner scattering processes is detected and evaluated by the detector arrangement. Since the X-radiation penetrates through the surface of the material at a characteristic depth of penetration, the scattered radiation back-scattered from the material sample thus contains information from the depth of the material sample, which information may be analyzed and assessed.

For this purpose, in an advantageous embodiment of the method, the scattered radiation is registered and spectrally evaluated by the detector arrangement in a multi-channel and energy-selective manner. Interactions between the radiation and the material are thus registered which are characteristic to the material structure and in particular to the substantial composition present in the material, whereby the weight per unit area and/or the chemical composition of the material may be determined.

Variations in the product position of a material sample leading to a positional shift of the scattered spot, in a further development of the method, are recorded by comparative measurements in a multi-component detector arrangement and are used for a measured-value correction. The measured-value correction is particularly necessary in high-speed conveyed material webs or sheet materials that have a considerable tendency to fluttering or waving caused by conveyance.

In an advantageous extension of the method according to the invention, the scattered radiation generated by the ambient atmosphere is detected, and from the detection result, environmental quantities are determined, in particular air temperature, air pressure or air humidity and are used for correcting the measurement result.

The scattered portion of the X-radiation may be either the general scattered radiation or the characteristic X-radiation generated within the sample, alone or in combination.

A device for determining a weight per unit area and/or a chemical composition of the material sample is characterized by a compact measurement head arranged unilaterally with respect to the material sample. This measurement head includes a radiation source for electromagnetic ionizing radiation which is directed to the material sample at an angle, and a multi-component detector arrangement disposed in a scattering angle and connected to a voltage supply and an evaluation unit. The radiation source is thus arranged so that the scattered radiation generated in the material sample is not delivered back into the radiation source but is transmitted in a selected spatial direction, and is detected there at an arbitrary distance from the radiation source without the radiation source directly influencing the detector.

Moreover, the measurement head has at least one environmental sensor, especially for pressure, temperature or humidity measurement. The measurement head is thus adapted for parallel measurements of environmental parameters influencing the measurement accuracy or the measurement results.

The detector arrangement may suitably be configured as a multi-channel, energy-sensitive count rate detector. Such a detector is suited for recording an energy spectrum and hence enables an elemental analysis of the material web.

Advantageously, the detector arrangement is formed of at least one first detector disposed with respect to the radiation source in a first scattering angle sensitive to the product position, and a second detector disposed with respect to the radiation source in a second scattering angle sensitive to the product position. The shifts of the scattered spot caused by variations of the product position are reflected by variable scattering angles, and are recorded by the first or second detector, with conclusions being allowed to be drawn as to the changed product position.

For the attachment of the device according to the invention, a transverse beam spanning the conveyor means for the material samples will suffice, from which only one side of the sheet material to be measured is detectable.

Appropriately, a radiation-absorbing screening means is arranged on the rear side of the material sample. This screening means has to be arranged so that scattered radiation exiting opposite to the direction of the incident ray may not be transmitted into the detector.

The method according to the invention and an exemplary embodiment of the measurement head according to the invention may be seen in the attached FIGURE.

The FIGURE shows a material sample 5, on the upper side of which a measurement head 10 is arranged. The measurement head has a base body 11, into which an X-radiation source 20 is integrated including shutters 21 and a detector arrangement 30. In addition, the measurement head has an arrangement of environmental sensors 40, by means of which environmental conditions, in particular the environmental quantities of pressure, temperature and air humidity in the immediate environment of the material sample 5 and/or the side of the measurement head facing the material sample may be determined. A voltage supply 51 for the X-ray source and a data acquisition unit 52 for the detector arrangement are likewise integrated into the measurement head. In this exemplary embodiment, the material sample is passed through below the measurement head by means of a conveyor installation. Moreover, the illustrated arrangement has an essentially radiation-impermeable screening means 70 on the lower side of the material sample.

The X-radiation is generated and emitted by the X-radiation source 20, e.g. in the form of X-ray bremsstrahlung, and is directed with a defined ray cross-section generated by the shutter arrangement 21 through a radiation window 12 onto the material sample 5. On the surface of the sample and in its interior, a certain portion of the incident radiation is scattered in a radiation spot 3 due to the interaction of various scattering processes within the probe, and is scattered back from the material sample in the direction of the measurement head 10. The scattering processes result on the one hand from the inherent nature of the material sample, in particular its density and hence its weight per unit area.

Furthermore, the impact of the X-radiation leads to a partial ionization of inner electron shells and resulting emissions of characteristic element-typical X-ray spectra, e.g. of the known K and L series having the element-typical wavelengths of the $K_\alpha$ or $L_\alpha$ lines. Under application of Moseley's law, an elemental analysis of the material sample is possible by evaluating these lines. Due to the large penetration capacity of the used X-radiation, usable signals may also be obtained from a greater material depth.

The detector arrangement detects the secondary backscattered X-radiation, and outputs the measurement signals on this occasion to an evaluation unit (not illustrated). Depending on the required use in each case, the detector arrangement 30 in each case may include components which vary depending on the kind of use, or the data acquisition unit 52 may be equipped for special evaluation processes of the delivered measurement signals. For measuring the weight per unit area, basically a simple counter arrangement operating independently from the X-ray photon energy, in the simplest case a counter tube arrangement, is suitable, the count rate of which is determined by the data acquisition unit. In general, the count rate of the scattered X-radiation is linearly dependent on the weight per unit area of the material sample.

Detection of the characteristic X-ray spectrum of the secondary scattered X-radiation requires an energy-sensitive count rate determining detector arrangement including an evaluation unit for determining the energy-dependent count rates. Such a detector arrangement may also be used for determining the gsm substance of the material sample. In this case, the evaluation unit is configured so that a total count rate as a sum is determined across all energy-dependent single count rates.

Effects arising due to the variation of the position of the material sample, the temperature, or by self-absorption are compensated for. By calibrating, using one or more calibrating etalons whose weight per unit area and/or chemical composition is known, a functional correlation between the weight per unit area and/or the chemical composition may be established. Knowledge of the original intensity of the primary X-radiation is not necessary. Only the constancy of the intensity of the incident radiation or knowledge of its temporal variation is of importance.

In the case of a general scattered radiation which, for an incident ray, consists of scattered Raleigh or Compton radiation, the intensity of the scattered portion depends essentially on the number of electrons within the material volume penetrated by the incident ray. This applies above all to materials having a similar chemical composition. The amount of scattered Raleigh and Compton radiation detected in the detector arrangement 30, with a constant radiation geometry is thus a measure for the weight per unit area of the material.

The intensity of the radiation scattered from the radiation spot, which develops due to characteristic radiation, strongly depends on the energy distribution of the incident radiation and the elemental composition of the measured material. With a detector arrangement 30, which is configured to be energy-selective and by means of which the scattered radiation is therefore measured spectrally, a conclusion may be drawn as to the presence of certain chemical elements in the sample.

If the geometry of the measurement arrangement varies, in particular the distance of the material to be measured to the detector arrangement, then the measurement value determining the amount of the radiation reaching the detector will thereby be changed. This principal error source of the measurement method may be minimized by a specific geometry of the radiation source, material web and detector arrangement, and may be eliminated to a certain extent.

For this purpose, the ray is directed onto the sheet material at an angle α. Variations of the distance between the measurement head and material web, in particular a vertical fluttering caused by the conveying process, cause a positional shift of the radiation spot on the sheet material. For detecting this changed measurement geometry, two single detectors 30a and 30b operating independently from each other are used as the detector arrangement 30. These are disposed so that a changed radiation spot position caused by variations of the product positions leads to a scattered ray incidence either on detector 30a or on detector 30b. By analyzing the different detector signals that change in a unique manner, the product position may thus be determined. For this purpose, the sum of both of the signals with a function obtained by calibration, and the quotient of the detector signals may be used. By an optimization, detector signals may also be found, in which the sum of the detector signals with sufficient accuracy within certain maximum values of the product position deviation, results in a value of the weight per unit area independent of the product position. In this case, the detectors are disposed symmetrically with respect to a plane defined by the direction of the primary ray.

Appropriately, the ray is directed at an angle to the material to be measured so that a narrow radiation spot is generated in the traversing direction. The vector following the direction of the incident ray then has a component in the direction of the traversing movement. Thereby, a local resolving power of the array is obtained.

For a penetrating radiation such as a hard energetic and hence an X-radiation of a shorter wavelength, the attenuation of the incident ray intensity and of the scattered radiation may be ignored in the material to be measured. In this case, the radiation amount detectable by the detector arrangement increases source-linearly with the material amount penetrated by rays. If the material thicknesses are high or if the portion of a chemical element is so large that a self-absorption becomes noticeable, a functional correlation may be determined between detector signal and weight per unit area through a calibration of the array using several calibrating etalons differing in the weight per unit area and/or the chemical composition.

The functional capability of the measurement method essentially depends on the temporally constant intensity of the incident ray. Variations in its energy distribution or intensity change the measured value-determining amount of the scattered radiation which is recorded in the detector. This leads to erroneous results in the weight per unit area and/or the chemical composition. By means of intermediate calibrations carried out at suitable time intervals using a specific calibrating etalon, a deviation of the intensity of the incident ray may be corrected.

For this purpose, the measurement head must be brought into a position where the incident ray falls onto the calibrating etalon instead of the material to be measured. The signal obtained in this position and the known weight per unit area and/or the chemical composition of the calibrating etalon in conjunction with the known functional correlation of both of the quantities permit a calibration correction corresponding to the instantaneous source strength.

An X-ray detector is also suitable for detecting environmental quantities, which will be used so that it detects only scattered radiation originating from scattering at atoms and molecules in the surroundings without signals being generated in the X-ray detector that arise from scattering processes within the sample. However, in this method, the constancy of the source strength of the incident ray must be ensured and permanently checked. In principle, this may also be done by means of an X-ray detector, which will be used so as to detect only scattered radiation originating from the scattering in a calibrating etalon that is present within the optical path of the incident ray during the measurements without signals being generated in it arising from scattering processes within the sample or from atoms or molecules in the surroundings.

The most important environmental quantity, the density of the air, may also be determined by measurement of the air temperature and air pressure. Since this method is independent of a constant intensity of the X-ray source, it does not need to be permanently checked in this case for determining the corrections.

Further embodiments will become clear from further developments of the shown exemplary embodiment within the scope of a skilled person's activity.

The invention claimed is:

1. A method for determining at least one of a weight per unit area and a chemical composition of a conveyed material sample, comprising:
providing a radiation source configured to emit an X-radiation;
irradiating a material sample with the X-radiation;

detecting a sample radiation scattered by the material sample and a radiation scattered by atmospheric particles; and analyzing the sample radiation and the radiation scattered by the atmospheric particles to determine at least one of a weight per unit area and a chemical composition of the material sample;

wherein the detection includes a recording by a multi-component detector arrangement, and a recording of a positional variation of the material sample by comparative measurements, and a measured value of at least one of the weight per unit area and the chemical composition obtained by the analyzing is corrected based on the positional variation of the material sample.

2. The method according to claim 1, wherein the irradiating includes directing the X-radiation emitted from the radiation source onto a scattered spot of the material sample, and the detecting includes detecting by the multi-component detector arrangement a radiation scattered at an inner portion of the material sample by inherent scattering.

3. The method according to claim 1 or 2, wherein the detecting includes recording and spectrally evaluating detected radiations in a multi-channel and energy-selective manner.

4. The method according to claim 1, wherein the detecting includes detecting a secondary back-scattered radiation of the X-radiation.

5. The method according to claim 1, wherein the detecting includes detecting a characteristic X-radiation of the X-radiation.

6. The method according to claim 1, wherein the detecting includes detecting a mixture of a general back-scattered radiation and a characteristic X-radiation of the X-radiation, and the chemical composition is determined based on energy spectrum of the characteristic X-radiation.

7. A method for determining at least one of a weight per unit area and a chemical composition of a conveyed material sample, comprising:

providing a radiation source configured to emit an X-radiation;

irradiating a material sample with the X-radiation;

detecting a sample radiation scattered by the material sample and a radiation scattered by atmospheric particles; and analyzing the sample radiation and the radiation scattered by the atmospheric particles to determine at least one of a weight per unit area and a chemical composition of the material sample;

wherein the detecting includes determining at least one of air temperature, air pressure and air humidity based on the radiation scattered by the atmospheric particles, and correcting a measured value of the weight per unit area.

8. A device for determining at least one of a weight per unit area and a chemical composition of a material sample, comprising:

a compact measurement head positioned on one side of a material sample, the compact measurement head including, a radiation source configured to emit electromagnetic ionizing radiation which is directed to the material sample at an angle, at lease one environmental sensor configured to detect a radiation scattered by atmospheric particles, and a multi-component detector arrangement configured to detect a sample radiation scattered by the material sample and connected to a voltage supply and an evaluation unit configured to evaluate the sample radiation and the radiation scattered by the atmospheric particles to determine at least one of a weight per unit area and a chemical composition of the material sample.

9. The device according to claim 8, wherein the at least one environmental sensor is configured to measure at least one of pressure, temperature and humidity of air.

10. The device according to any one of claim 8 or 9, wherein the detector arrangement comprises a multi-channel energy-sensitive count rate detector.

11. The device according to claim 9, wherein the at least one environmental sensor is configured to determine an air density by detecting the radiation incident from surroundings of the measurement head.

12. The device according to claim 8, wherein the detector arrangement comprises at least one first detector disposed with respect to the radiation source in a first scattering angle and configured to be sensitive to a positional variation of the material sample, and a second detector disposed with respect to the radiation source in a second scattering angle and configured to be sensitive to the positional variation.

13. The device according to claim 8, further comprising a conveyor configured to transfer the material sample, the conveyor having a transverse beam on which the measurement head is disposed.

14. The device according to claim 8, further comprising a radiation-absorbing screening unit positioned on a rear side of the material sample and configured to absorb a scattered radiation exiting from the rear side of the material sample.

* * * * *

UNITED STATES PATENT AND TRADEMARK OFFICE
CERTIFICATE OF CORRECTION

PATENT NO. : 7,242,747 B2  Page 1 of 1
APPLICATION NO. : 10/968327
DATED : July 10, 2007
INVENTOR(S) : Zerle It is certified that error appears in the above-identified patent and that said Letters Patent is hereby corrected as shown below:

On the title page, Item (54), and Column 1, the title is incorrect. Item (54) should read:

-- (54) A METHOD FOR DETERMINING A WEIGHT PER UNIT AREA AND/ OR A CHEMICAL COMPOSITION OF A CONVEYED MATERIAL SAMPLE, AND A DEVICE FOR THIS PURPOSE --

Signed and Sealed this

Twenty-eighth Day of August, 2007

JON W. DUDAS
*Director of the United States Patent and Trademark Office*